(12) United States Patent
Berens et al.

(10) Patent No.: US 7,270,804 B2
(45) Date of Patent: Sep. 18, 2007

(54) USE OF ONE OR SEVERAL SUBSTANCES SELECTED FROM THE GROUP OF PYRIMIDINES AND PURINES IN COSMETIC PREPARATIONS FOR TANNING THE SKIN

(75) Inventors: Werner Berens, Chevy Chase, MD (US); Rainer Wolber, Hamburg (DE); Christoph Smuda, Bönningstedt (DE); Jan Batzer, Hamburg (DE); Claudia Mundt, Bremen (DE); Franz Stäb, Echem (DE); Thomas Blatt, Wedel (DE)

(73) Assignee: Beiersdorf AG, Hamburg (DE)

( * ) Notice: Subject to any disclaimer, the term of this patent is extended or adjusted under 35 U.S.C. 154(b) by 398 days.

(21) Appl. No.: 10/820,874

(22) Filed: Apr. 9, 2004

(65) Prior Publication Data

US 2004/0265250 A1 Dec. 30, 2004

Related U.S. Application Data

(63) Continuation of application No. PCT/EP02/11157, filed on Oct. 4, 2002.

(30) Foreign Application Priority Data

Oct. 11, 2001 (DE) ................ 101 50 412

(51) Int. Cl.
*A61Q 19/04* (2006.01)
*A61Q 17/00* (2006.01)
*A01N 43/54* (2006.01)

(52) U.S. Cl. .............. 424/59; 424/60; 424/400; 424/401; 514/256; 514/261

(58) Field of Classification Search .......... 424/59, 424/60, 400, 401; 514/256, 261
See application file for complete search history.

(56) References Cited

U.S. PATENT DOCUMENTS

| 5,075,102 A | 12/1991 | Hubaud et al. |
| 5,470,577 A | 11/1995 | Gilchrest et al. |
| 5,470,579 A | 11/1995 | Bonte et al. |
| 5,476,651 A | 12/1995 | Meybeck et al. |
| 5,540,914 A | 7/1996 | Fuller |
| 5,554,359 A | 9/1996 | Fuller |
| 5,589,161 A | 12/1996 | Fuller |
| 5,591,423 A | 1/1997 | Fuller |
| 5,628,987 A | 5/1997 | Fuller |
| 5,643,556 A | 7/1997 | Gilchrest et al. |
| 5,998,423 A | 12/1999 | Manneth et al. |
| 6,116,281 A | 9/2000 | Mastromatteo |
| 6,380,263 B1 | 4/2002 | Pruche et al. |
| 6,399,046 B1 | 6/2002 | Schönrock et al. |
| 6,623,725 B2 | 9/2003 | Golz-Berner et al. |
| 6,706,696 B1 * | 3/2004 | Griesbach et al. ............ 514/54 |
| 2002/0103216 A1 | 8/2002 | Pruche et al. |
| 2003/0082119 A1 | 5/2003 | Golz-Berner et al. |

FOREIGN PATENT DOCUMENTS

| DE | 82806 | 6/1971 |
| DE | 10015363 | 10/2001 |
| EP | 0829260 | 3/1998 |
| WO | 91/07945 | 6/1991 |
| WO | 92/20322 | 11/1992 |
| WO | 95/01773 | 1/1995 |
| WO | 98/12212 | 3/1998 |
| WO | 99/66897 | 12/1999 |

OTHER PUBLICATIONS

Harry's Cosmetology, 7th edition, Chemical Publishing New York, pp. 431-432.

Hadshiew I.M., Eller M.S., Gasparro F.P., Gilchrest B.A., "Stimulation of melanogenesis by DNA oligonucleotides: effect of size, sequence and 5'phosphorylation" Journal of Dermatological Science, 2001, 25, pp. 127-138.

* cited by examiner

*Primary Examiner*—Shelley A. Dodson
(74) *Attorney, Agent, or Firm*—Greenblum & Bernstein, P.L.C.

(57) ABSTRACT

Use of one or more substances selected from the group of pyrimidines and purines for the preparation of cosmetic or dermatological preparations for boosting natural skin tanning and/or for stimulating melanogenesis in human skin.

40 Claims, No Drawings

USE OF ONE OR SEVERAL SUBSTANCES SELECTED FROM THE GROUP OF PYRIMIDINES AND PURINES IN COSMETIC PREPARATIONS FOR TANNING THE SKIN

CROSS-REFERENCE TO RELATED APPLICATIONS

The present application is a continuation of International Application No. PCT/EP02/11157, filed Oct. 4, 2002, the entire disclosure whereof is expressly incorporated by reference herein, which claims priority under 35 U.S.C. § 119 of German Patent Application No. 101 50 412.8, filed Oct. 11, 2001.

BACKGROUND OF THE INVENTION

1. Field of the Invention

The present invention relates to cosmetic and dermatological preparations for tanning the skin, in particular to those which also offer protection against UV radiation.

2. Discussion of Background Information

The harmful effect of the ultraviolet part of solar radiation on the skin is generally known. While rays having a wavelength of less than 290 nm (the UVC region), are absorbed by the ozone layer in the earth's atmosphere, rays in the range between 290 nm and 320 nm, the UVB region, cause erythema, simple sunburn or even burns of varying severity.

The erythema activity maximum of sunlight is given as the relatively narrow region around 308 nm.

Numerous compounds are known for protecting against UVB radiation; these are mostly derivatives of 3-benzylidenecamphor, of 4-aminobenzoic acid, of cinnamic acid, of salicylic acid, of benzophenone and also of 2-phenylbenzimidazole.

It is also important to have available filter substances for the range between about 320 nm and about 400 nm, the UVA region, since its rays can also cause damage. Thus, it has been found that UVA radiation leads to damage of the elastic and collagenous fibers of connective tissue, causing premature aging of the skin, and that it is to be regarded as a cause of numerous phototoxic and photoallergic reactions. The harmful effect of UVB radiation can be intensified by UVA radiation.

In addition, UVA radiation can cause skin damage by damaging keratin or elastin in the skin. This leads to a reduction in elasticity and water-storage capacity of the skin, i.e. the skin becomes less supple and tends towards wrinkling. The notably high incidence of skin cancer in regions where solar irradiation is strong indicates that damage to the genetic information in cells is also apparently caused by sunlight.

However, UV radiation can also lead to photochemical reactions, the photochemical reaction products intervening in the skin's metabolism.

Such photochemical reaction products are predominantly free-radical compounds, e.g. hydroxyl radicals. Undefined free-radical photoproducts which are formed in the skin itself can also display uncontrolled secondary reactions as a result of their high reactivity. However, singlet oxygen, a non-free-radical excited state of the oxygen molecule, can also arise during UV irradiation, as can short-lived epoxides and many others. Singlet oxygen, for example, differs from the normal triplet oxygen (free-radical ground state) by virtue of its increased reactivity. However, excited, reactive (free-radical) triplet states of the oxygen molecule also exist.

UV radiation is also a type of ionizing radiation. There is therefore the risk that ionic species may also arise during UV exposure, which then, for their part, are capable of oxidative intervention in the biochemical processes.

The pigmentation of human skin is essentially brought about by the presence of melanin. Melanin and its degradation products (melanoids), carotene, degree of perfusion, and the condition and thickness of the Stratum corneum and other skin layers permit skin shades from virtually white (in cases of reduced filling or in cases of an absence of blood vessels) or yellowish via pale brown-reddish, bluish to brown of different shades and finally almost black. The individual regions of the skin display differing depths of shade as a result of varying amounts of melanin.

Natural melanin protects the skin from penetrating UV radiation. The number of melanin granules produced in the melanocytes determines whether a person has pale skin or dark skin. In cases of strong pigmentation (e.g. in colored races, but also in those with pale skin following UV irradiation) melanin is also to be found in the Stratum spinosum and even in the Stratum corneum. It attenuates the UV radiation by up to about 90% before it reaches the corium.

As characteristic cell organelles, melanocytes contain melanosomes in which the melanin is formed. Upon excitation by UV radiation, inter alia, melanin is formed to an increased degree. This is transported via the living layers of the epidermis (keratinocytes) ultimately to the horny layer (corneocytes) and causes the more or less marked brownish to brown-black skin color. Melanin is formed as the final stage of an oxidative process in which tyrosine converts, with the assistance of the enzyme tyrosinase, via several intermediates to the brown to brown-black eumelanins (DHICA and DHI melanin) and/or, with participation of sulfur-containing compounds, to the reddish pheomelanin. DHICA and DHI melanins arise via the common intermediate stages dopaquinone and dopachrome. The latter is converted, partially with participation of further enzymes, either into indole-5,6-quinonecarboxylic acid or into indole-5,6-quinone, from which the two specified eumelanins form. The formation of pheomelanin proceeds, inter alia, via the intermediate products dopaquinone and cysteinyldopa.

Besides various functions of the skin's own melanin (also "detoxification"/binding of toxic substances/pharmaceuticals etc.), the function of melanin as a natural UV filter to protect against harmful UV rays, and the antioxidant function of melanin as protection against reactive oxygen species (oxidative stress), which may arise, inter alia, as a result of solar irradiation, is very important for skin, inter alia with regard to homeostasis, prevention of skin aging, prevention of sunburn etc. This thus gives rise not only to a cosmetic benefit in the sense of enhanced tanning as a result of the increased synthesis of melanin in the skin following topical application of the active ingredient according to the invention, but also an additional protection as a result of the various protective powers of melanin.

Depending on their sensitivity to light, the skin types below are normally differentiated:

| | |
|---|---|
| Skin type I | never tans, always burns. |
| Skin type II | rarely tans, burns easily. |
| Skin type III | tans averagely well. |
| Skin type IV | tans easily to give a lasting tan, almost never burns. |
| Skin type V | dark, often almost black skin, never burns. |

The natural shielding from harmful UV radiation is a tangible advantage of natural skin tanning. Moreover, for many decades a "healthy" skin color has been a sign of, in particular, sporting activity and is therefore considered to be desirable by a broad section of consumers. Representatives of skin types I and II who wish to enjoy such a skin shade in any case therefore have to rely on self-tanning preparations. However, representatives of skin type III who do not wish to excessively be exposed to the risks of sunbathing but nevertheless want to appear tanned are also thankful target groups for self-tanning preparations.

Artificial skin tanning can be brought about in a cosmetic or medicinal way, the following approaches essentially playing a role:

The regular taking of carotene preparations results in carotene being stored in the subcutaneous fatty tissue, and the skin gradually turns orange to yellow-brown.

Using make-up preparations which can be washed off it is possible to achieve a slight skin shading (e.g. extracts of fresh green walnut shells, henna).

Coloring can also take place via the route of a chemical change in the horny layer of the skin using self-tanning preparations. The most important active ingredient is dihydroxyacetone (DHA). The skin tanning achieved in this way cannot be washed off and is removed only with the normal flaking of the skin (after about 10-15 days). Dihydroxyacetone can be referred to as ketotriose and reacts as a reducing sugar with the amino acids of the skin and the free amino and imino groups of keratin via a number of intermediates in the sense of a Maillard reaction to give brown-colored substances, so-called melanoids, which are sometimes also called melanoidins.

A disadvantage of tanning with dihydroxyacetone is that the skin tanned therewith is not protected from sunburn, in contrast to "sun-tanned" skin.

A further disadvantage of dihydroxyacetone is that, particularly under the influence of ultraviolet radiation, formaldehyde is eliminated, albeit in small amounts in most cases.

There was a need to find ways in which the decomposition of dihydroxyacetone can be effectively countered.

Coloration by means of self-tanning compositions takes place without exposure to sunlight. In contrast to this, so-called pre-tan products or tan promoters are also offered, which have to be applied prior to exposure to the sun. In the sun, a yellowing of these preparations then arises, which is said to lead to a slight brown-yellow coloration of the outer skin, which additionally enhances the "suntan".

A further type of artificial tanning which is likewise completely independent of UV light can be brought about by the hormones which are usually released within the body also as a result of (natural) UV exposure and ultimately stimulate the melanocytes to synthesize melanin. In this connection, mention may be made, for example, of modifications of proopiomelanocortin (POMC), such as aMSH and synthetic variants (such as NDP), some of which have much higher activity than the natural aMSH. Although tanning can in principle be brought about by these hormones, their use in cosmetics is not possible since they are clearly pharmacologically effective substances (hormones) which should not be used widely without medicinal indication.

It was surprising and could not have been foreseen by the person skilled in the art that the use of one or more substances chosen from the group of pyrimidines and purines for boosting natural skin tanning and/or for stimulating melanogenesis in human skin may overcome the disadvantages of the prior art.

SUMMARY OF THE INVENTION

The present invention provides a cosmetic or dermatological composition for boosting natural skin tanning and/or stimulating melanogenesis in human skin. The composition comprises from 0.0001% to 20% by weight of at least one substance which is selected from pyrimidines and purines.

In one aspect of the composition, the at least one substance may be present in a concentration of from 0.001% to 10% by weight, e.g., in a concentration of from 0.01% to 1% by weight.

In another aspect, the composition may comprise at least one of purine, uracil, thymine, adenine, guanine and cytosine. In yet other aspects, the composition may comprise purine, or it may comprise uracil, or it may comprise thymine, or it may comprise adenine, or it may comprise guanine, or it may comprise cytosme.

In as still further aspect, the composition may comprise at least 0.1% by weight of uracil.

In yet another aspect, the composition may further comprise a UVA filter and/or a UVB filter.

In another aspect, the composition may further comprise an inorganic pigment, for example, an oxide of Ti, Zn, Fe, Zr, Si, Mn, Al and/or Ce such as, e.g., $TiO_2$. For example, the composition may comprise from 0.5% to 6% by weight of an inorganic pigment.

In yet another aspect, the composition may further comprise a hydrophobic inorganic micropigment.

In yet another aspect, the composition may further comprise from 0.05% to 10% by weight of an antioxidant.

The present invention also provides a sunscreen, an O/W cream, a W/0 emulsion and a gel cream which comprises the composition of the present invention, including the various aspects thereof.

The present invention also provides a method for boosting natural skin tanning and/or stimulating melanogenesis in human skin. This method comprises the application of a composition which comprises at least one substance that is selected from pyrimidines and purines onto at least parts of the skin.

In one aspect of this method, the at least one substance may be present in a concentration of from 0.0001% to 20% by weight, preferably in a concentration of from 0.01% to 1% by weight.

In another aspect of the method, the composition may comprise at least one of purine, uracil, thymine, adenine, guanine and cytosine.

In a still further aspect of the method, the composition may comprise at least 0.1% by weight of uracil.

In another aspect, the composition may comprise an emulsion.

In yet another aspect of the method, the method may comprise the treatment of hypopigmentation.

A particular advantage is that, as a result of the present invention, physiological processes (increased synthesis of melanin) of the skin are utilized in order to obtain desired tanning of the skin, and as a result of this the intrinsic protection of the skin is improved (various protective powers of melanin). The activation of the skin's own tanning can of course take place with and without the involvement of UV light.

Purines represent a group of important compounds which are widespread in nature and participate in human, animal, plant and microbial metabolic processes, and which derive from the parent substance purine through substitution by OH, $NH_2$, SH in the 2, 6 and 8 position and/or by $CH_3$ in the 1, 3, 7 position.

The basic framework of purine and its derivatives is characterized by the following structure:

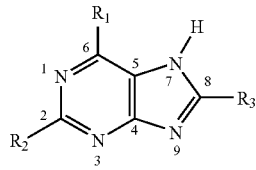

| | $R_1$ | $R_2$ | $R_3$ |
|---|---|---|---|
| Purine | H | H | H |
| Adenine | $NH_2$ | H | H |
| Guanine | OH | $NH_2$ | H |
| Uric acid | OH | OH | OH |
| Hypoxanthine | OH | H | H |
| Purinethiol | SH | H | H |
| 6-Thioguanine | SH | $NH_2$ | H |
| 6-Xanthine | OH | OH | H |

The biosynthesis of the purine takes place at the nucleotide stage from glycine and $CO_2$, and small molecular fragments of L-glutamine, of L-aspartic acid and of 10-formyltetrahydrofolic acid. In metabolism, purine bases are released which are partly reutilized in the cells, i.e. converted into one another.

The most important purines include adenine and guanine which—together with the pyrimidines uracil, thymine and cytosine—are constituents of nucleic acids, also hypoxanthine, xanthine and uric acid as metabolic products of humans and animals, and the plant purines, often referred to as purine alkaloids, caffeine, theobromine and theophylline, which are present in coffee, cocoa and tea.

Plant growth substances which likewise belong to the purines are zeatin and kinetin (cytokinins). Among the animal foodstuffs, the innards, particularly thymus, are rich in purines, and fish and green peas also contain relatively large amounts.

For the purposes of the present invention, pyrimidines are the derivatives of pyrimidine

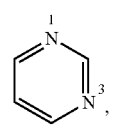

cytosine

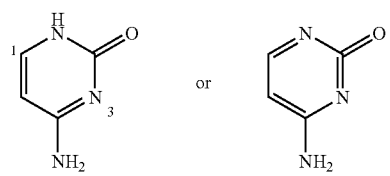

or uracil

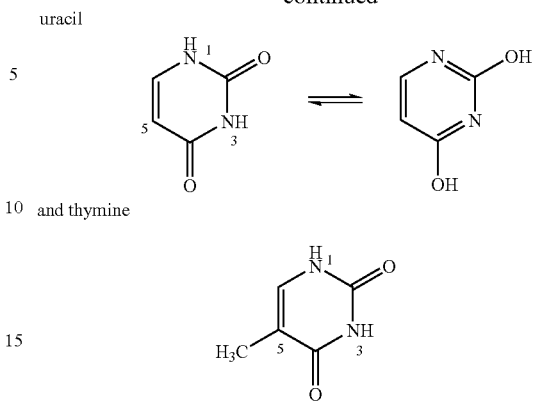

and thymine

Cytosine and thymine are counterparts of adenine and guanine in deoxyribonucleic acid. The role of cytosine is taken over by uracil in ribonucleic acid.

Surprisingly, it has been found that one or more substances chosen from the group of pyrimidines and purines increase the activity of the melanocytes of the human skin and thus also melanogenesis as a physiological process and as a result enhance natural skin tanning.

Skincare products according to the invention advantageously comprise 0.0001-20 percent by weight of one or more substances chosen from the group of pyrimidines and purines, preferably purine and/or uracil and/or thymine and/or adenine and/or guanine and/or cytosine.

Cosmetic or dermatological preparations according to the invention preferably comprise 0.001-10% by weight of one or more substances chosen from the group of pyrimidines and purines, based on the total composition of the preparations.

Cosmetic or dermatological preparations according to the invention very particularly preferably comprise 0.01-1% by weight of one or more substances chosen from the group of pyrimidines and purines, based on the total composition of the preparations.

According to the invention the cosmetic and/or dermatological light protection formulations can have the customary composition and be used for cosmetic and/or dermatological light protection, and also for the treatment, care and cleansing of skin and/or hair and as a make-up product in decorative cosmetics.

For use, the cosmetic and dermatological preparations according to the invention are applied to the skin and/or hair in sufficient amount and in the manner conventional for cosmetics.

Particularly preferred cosmetic and dermatological preparations are those which are in the form of a sunscreen. Advantageously, these can additionally comprise at least one further UVA filter and/or at least one further UVB filter and/or at least one inorganic pigment, preferably an inorganic micropigment.

Surprisingly, cosmetic and dermatological preparations according to the invention are able to prolong natural tanning.

In addition, it was surprising that cosmetic and dermatological formulations according to the invention are able to serve for the treatment of hypopigmentations (vitiligo, uneven pigmentation in aging skin etc.).

According to the invention the cosmetic and dermatological preparations can comprise cosmetic auxiliaries such as those conventionally used in such preparations, e.g. preservatives, bactericides, perfumes, antifoams, dyes, pigments which have a coloring effect, thickeners, moisturizers and/or humectants, fats, oils, waxes or other conventional constituents of a cosmetic or dermatological formulation, such as alcohols, polyols, polymers, foam stabilizers, electrolytes, organic solvents or silicone derivatives.

An additional content of antioxidants is generally preferred. According to the invention, favorable antioxidants which can be used are any antioxidants suitable or customary for cosmetic and/or dermatological applications.

It is also advantageous to add antioxidants to the preparations according to the invention. The antioxidants are advantageously selected from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximines) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

The amount of the abovementioned antioxidants (one or more compounds) in the preparations is preferably from 0.001 to 30% by weight, particularly preferably from 0.05 to 20% by weight, especially 1-10% by weight, based on the total weight of the preparation.

If vitamin E and/or derivatives thereof are used as the antioxidant or antioxidants, their respective concentrations are advantageously chosen from the range of 0.001-10% by weight, based on the total weight of the formulation.

If vitamin A or vitamin A derivatives or carotenes or derivatives thereof are used as the antioxidant or antioxidants, their respective concentrations are advantageously chosen from the range of 0.001-10% by weight, based on the total weight of the formulation.

The lipid phase can advantageously be chosen from the following group of substances:
mineral oils, mineral waxes
oils, such as triglycerides of capric or caprylic acid, but preferably castor oil;
fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;
alkyl benzoates;
silicone oils such as dimethylpolysiloxanes, diethylpolysiloxanes, diphenylpolysiloxanes and mixtures thereof.

For the purposes of the present invention, the oil phase of the emulsions, oleogels and hydrodispersions or lipodispersions is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Such ester oils can advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semisynthetic and natural mixtures of such esters, e.g. jojoba oil.

The oil phase can also advantageously be chosen from the group of branched and un-branched hydrocarbons and hydrocarbon waxes, silicone oils, dialkyl ethers, from the group of saturated or unsaturated, branched or unbranched alcohols, and also fatty acid triglycerides, namely the triglycerol esters of saturated and/or unsaturated, branched and/or unbranched alkanecarboxylic acids having a chain length of from 8 to 24, in particular 12-18, carbon atoms. The fatty acid triglycerides can advantageously be chosen, for example, from the group of synthetic, semisynthetic and natural oils, e.g. olive oil, sunflower oil, soybean oil, peanut oil, rapeseed oil, almond oil, palm oil, coconut oil, palm kernel oil and the like.

For the purposes of the present invention, any mixtures of such oil and wax components can also advantageously be used. When required, it can also be advantageous to use waxes, for example. cetyl palmitate, as the sole lipid component of the oil phase.

The oil phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicaprylyl ether.

Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous.

Of the hydrocarbons, paraffin oil, squalane and squalene are advantageously to be used for the purposes of the present invention.

The oil phase can advantageously also contain cyclic or linear silicone oils or can consist entirely of such oils, although it is preferable to use an additional content of other oil phase components in addition to the silicone oil or silicone oils.

Cyclomethicone (octamethylcyclotetrasiloxane) is advantageously used as the silicone oil to be used according to the invention. However, other silicone oils can also advantageously be used for the purposes of the present invention, for example hexamethylcyclotrisiloxane, polydimethylsiloxane, poly(methylphenylsiloxane).

Mixtures of cyclomethicone and isotridecyl isononanoate and mixtures of cyclomethicone and 2-ethylhexyl isostearate are also particularly advantageous.

The aqueous phase of the preparations according to the invention may advantageously comprise
alcohols, diols or polyols of low carbon number, and also their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol, and especially one or more thickeners which can advantageously be selected from the group consisting of silicon dioxide, aluminum silicates and polysaccharides and derivatives thereof, e.g. hyaluronic acid, xanthan gum, hydroxypropylmethylcellulose, and particularly advantageously from the group of polyacrylates, preferably a polyacrylate from the group consisting of the so-called Carbopols, for example Carbopol grades 980, 981, 1382, 2984, 5984, in each case individually or in combination.

The preparations according to the invention can advantageously also comprise substances which absorb UV radiation in the UVB region, the total amount of the filter substances being, for example, 0.1% by weight to 30% by weight, preferably 0.5 to 10% by weight, in particular 1.0 to 6.0% by weight, based on the total weight of the preparations, in order to provide cosmetic preparations which protect the hair and/or skin from the entire region of ultraviolet radiation. They can also serve as sunscreens for the hair.

If the preparations according to the invention comprise UVB filter substances, these may be oil-soluble or water-soluble. Examples of oil-soluble UVB filters which are advantageous according to the invention are:
3-benzylidenecamphor derivatives, preferably 3-(4-methylbenzylidene)camphor, 3-benzylidenecamphor;
4-aminobenzoic acid derivatives, preferably 2-ethylhexyl 4-(dimethylamino)benzoate, amyl 4-(dimethylamino) benzoate;
esters of cinnamic acid, preferably 2-ethylhexyl 4-methoxycinnamate, isopentyl 4-methoxycinnamate;
esters of salicylic acid, preferably 2-ethylhexyl salicylate, 4-isopropylbenzyl salicylate, homomenthyl salicylate,
derivatives of benzophenone, preferably 2-hydroxy-4-methoxybenzophenone, 2-hydroxy-4-methoxy-4'-methylbenzophenone, 2,2'-dihydroxy-4-methoxybenzophenone;
esters of benzalmalonic acid, preferably di(2-ethylhexyl) 4-methoxybenzalmalonate,
2,4,6-trianilino(p-carbo-2'-ethyl-1'-hexyloxy)-1,3,5-triazine.

Examples of advantageous water-soluble UVB filters are:
salts of 2-phenylbenzimidazole-5-sulfonic acid, such as its sodium, potassium or its triethanolammonium salt, and the sulfonic acid itself;
sulfonic acid derivatives of benzophenones, preferably 2-hydroxy-4-methoxybenzophenone-5-sulfonic acid and its salts;
sulfonic acid derivatives of 3-benzylidenecamphor, such as e.g. 4-(2-oxo-3-bornylidenemethyl)benzenesulfonic acid, 2-methyl-5-(2-oxo-3-bornylidenemethyl)sulfonic acid and its salts, and 1,4-di(2-oxo-10-sulfo-3-bornylidenemethyl)benzene and salts thereof (the corresponding 10-sulfato compounds, for example the corresponding sodium, potassium or triethanolammonium salt), also referred to as benzene-1,4-di(2-oxo-3-bornylidenemethyl-10-sulfonic acid.

The list of said UVB filters which can be used in combination with the active ingredient combinations according to the invention is not of course intended to be limiting.

It may also be advantageous to use UVA filters which are customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The amounts which can be used are those used for the UVB combination.

The total amount of dibenzoylmethanes, in particular 4-(tert-butyl)-4'-methoxydibenzoylmethane in the finished cosmetic or dermatological preparations is advantageously chosen from the range 0.1-10.0% by weight, preferably 0.5-6.0% by weight, based on the total weight of the preparations.

The total amount of camphor derivatives, in particular 4-methylbenzylidenecamphor and/or benzylidenecamphor, in the finished cosmetic or dermatological preparations is advantageously chosen from the range 0.1-10.0% by weight, preferably 0.5-6.0% by weight, based on the total weight of the preparations.

The total amount of triazine derivatives, in particular tris(2-ethylhexyl) 4,4',4''-(1,3,5-triazine-2,4,6-triyltriimino) trisbenzoate, in the finished cosmetic or dermatological preparations is advantageously chosen from the range 0.1-10.0% by weight, preferably 0.5-6.0% by weight, based on the total weight of the preparations.

Cosmetic and dermatological preparations according to the invention also advantageously comprise, although it is not obligatory, inorganic pigments based on metal oxides and/or other metal compounds which are insoluble or virtually insoluble in water, in particular the oxides of titanium ($TiO_2$), Zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals and mixtures of such oxides. Particular preference is given to pigments based on $TiO_2$.

According to the invention, the inorganic pigments are in hydrophobic form, i.e. they have been surface-treated to repel water. This surface treatment may involve providing the pigments with a thin hydrophobic layer by methods known per se.

One such method involves, for example, producing the hydrophobic surface layer by a reaction in accordance with

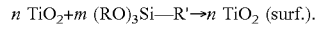

$n$ $TiO_2 + m$ $(RO)_3Si\text{—}R' \rightarrow n$ $TiO_2$ (surf.).

Here, n and m are stoichiometric parameters to be used as desired, and R and R' are the desired organic radicals. For example, hydrophobicized pigments prepared analogously to DE-A 33 14 742 are advantageous.

Advantageous $TiO_2$ pigments are available, for example, under the trade names T 805 from Degussa.

The total amount of inorganic pigments, in particular hydrophobic inorganic micro pigments, in the finished cosmetic or dermatological preparations is advantageously chosen from the range 0.1-30% by weight, preferably 0.1-10.0, in particular 0.5-6.0% by weight, based on the total weight of the preparations.

In addition, according to the invention it may optionally be advantageous to provide the preparations with further UVA and/or UVB filters, for example certain salicylic acid derivatives such as

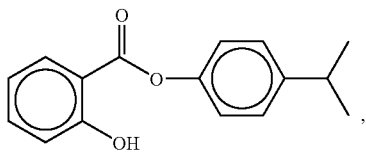

(4-isopropylbenzyl salicylate)

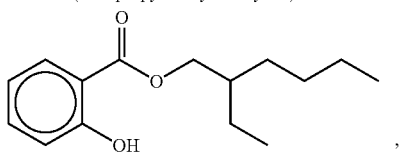

(2-ethylhexyl salicylate, octyl salicylate)

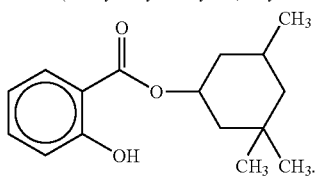

(homomenthyl salicylate)

The total amount of one or more salicylic acid derivatives in the finished cosmetic or dermatological preparations is advantageously chosen from the range 0.1-15.0% by weight, preferably 0.5-8.0% by weight, based on the total weight of the preparations. If ethylhexyl salicylate is chosen, it is advantageous to choose the total amount thereof from the range 0.1-5.0% by weight, preferably 0.5-2.5% by weight. If homomenthyl salicylate is chosen, it is advantageous to choose the total amount thereof from the range 0.1-10.0% by weight, preferably 0.5-5.0% by weight.

Another further additional light protection filter substance which is to be used advantageously in accordance with the invention is ethylhexyl 2-cyano-3,3-diphenylacrylate (octocrylene), which is available from BASF under the name UVINUL® N 539 and is characterized by the following structure:

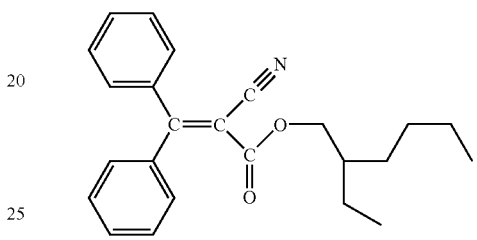

DETAILED DESCRIPTION OF THE INVENTION

The examples below serve to illustrate the present invention without limiting it. Unless stated otherwise, all amounts, proportions and percentages are based on the weight and the total amount or on the total weight of the preparations.

| I. Examples of O/W creams | | | | | |
|---|---|---|---|---|---|
| | Examples | | | | |
| | 1 | 2 | 3 | 4 | 5 |
| Glyceryl stearate citrate | | | 2.00 | | 2.00 |
| Glyceryl stearate, self-emulsifying | 4.00 | 3.00 | | | |
| PEG-40 stearate | 1.00 | | | | |
| Polyglyceryl-3-methylglucose distearate | | | | 3.00 | |
| Sorbitan stearate | | | | | 2.00 |
| Stearic acid | | 1.00 | | | |
| Stearyl alcohol | | | 5.00 | | |
| Cetyl alcohol | 3.00 | 2.00 | | 3.00 | |
| Cetylstearyl alcohol | | | | | 2.00 |
| Caprylic/capric triglyceride | 5.00 | 3.00 | 4.00 | 3.00 | 3.00 |
| Octyldodecanol | | | 2.00 | | 2.00 |
| Dicaprylyl ether | | 4.00 | | 2.00 | 1.00 |
| Paraffinum liquidum | 5.00 | 2.00 | | 3.00 | |
| Titanium dioxide | | | 1.00 | | |
| 4-Methylbenzylidenecamphor | | | 1.00 | | |
| 1-(4-tert-Butylphenyl)-3-(4-methoxyphenyl)-1,3-propanedione | | | 0.50 | | |
| Uracil | 0.50 | 0.20 | 0.10 | 1.00 | 0.30 |
| Tocopherol | 0.1 | | | | 0.20 |
| Biotin | | | 0.05 | | |
| Na₃HEDTA | 0.1 | | 0.10 | 0.1 | |
| Preservative | q.s. | q.s. | q.s. | q.s. | q.s. |
| Xanthan gum | | | | | |
| Polyacrylic acid | 3.00 | 0.1 | | 0.1 | 0.1 |
| Sodium hydroxide solution 45% | q.s | q.s. | q.s. | q.s. | q.s. |
| Glycerol | 5.00 | 3.00 | 4.00 | 3.00 | 3.00 |

-continued

| | | | | | |
|---|---|---|---|---|---|
| Butylene glycol | | 3.00 | | | |
| Perfume | q.s. | q.s. | q.s. | q.s. | q.s. |
| Water | ad 100 | ad 100 | ad 100 | ad 100 | ad 100 |

II. Examples of O/W creams

| | Examples | | | | |
|---|---|---|---|---|---|
| | 6 | 7 | 8 | 9 | 10 |
| Glyceryl stearate citrate | | 2.00 | 2.00 | | |
| Glyceryl stearate, self-emulsifying | 5.00 | | | | |
| Stearic acid | | | | 2.50 | 3.50 |
| Stearyl alcohol | 2.00 | | | | |
| Cetyl alcohol | | | | 3.00 | 4.50 |
| Cetyl stearyl alcohol | | 3.00 | 1.00 | | 0.50 |
| $C_{12-15}$-alkyl benzoate | | 2.00 | 3.00 | | |
| Caprylic/capric triglyceride | 2.00 | | | | |
| Octyldodecanol | 2.00 | 2.00 | | 4.00 | 6.00 |
| Dicaprylyl ether | | | | | |
| Paraffinum liquidum | | 4.00 | 2.00 | | |
| Cyclic dimethylpolysiloxane | | | | 0.50 | 2.00 |
| Dimethicone polydimethylsiloxane | 2.00 | | | | |
| Titanium dioxide | 2.00 | | | | |
| 4-Methylbenzylidenecamphor | 1.00 | | | | 1.00 |
| 1-(4-tert-Butylphenyl)-3-(4-methoxyphenyl)-1,3-propanedione | 0.50 | | | | 0.50 |
| Uracil | 0.15 | 0.75 | 0.25 | 1.00 | 0.40 |
| Tocopherol | | | | | 0.05 |
| $Na_3HEDTA$ | | | 0.20 | | 0.20 |
| Preservative | q.s. | q.s. | q.s. | q.s. | q.s. |
| Xanthan gum | | | 0.20 | | |
| Polyacrylic acid | 0.15 | 0.1 | | 0.05 | 0.05 |
| Sodium hydroxide solution 45% | q.s. | q.s. | q.s. | q.s. | q.s. |
| Glycerol | 3.00 | | 3.00 | 5.00 | 3.00 |
| Butylene glycol | | 3.00 | | | |
| Ethanol | | 3.00 | | 3.00 | |
| Perfume | q.s. | q.s. | q.s. | q.s. | q.s. |
| Water | ad 100 | ad 100 | ad 100 | ad 100 | ad 100 |

III. Examples of W/O emulsions

| | 1 | 2 | 3 | 4 | 5 |
|---|---|---|---|---|---|
| Cetyldimethicone copolyol | | 2.50 | | 4.00 | |
| Polyglyceryl-2 dipolyhydroxystearate | 5.00 | | | | 4.50 |
| PEG-30 dipolyhydroxystearate | | | 5.00 | | |
| 2-Ethylhexyl methoxycinnamate | | 8.00 | | 5.00 | 4.00 |
| 2,4-Bis(4-(2-ethylhexyloxy)-2-hydroxy)-phenyl)-6-(4-methoxyphenyl)-(1,3,5)-triazine | 2.00 | 2.50 | | 2.00 | 2.50 |
| 1-(4-tert-Butylphenyl)-3-(4-methoxyphenyl)-1,3-propanedione | | | 2.00 | 1.00 | |
| Diethylhexylbutamidotriazone | 3.00 | 1.00 | | | 3.00 |
| Ethylhexyltriazone | | | 3.00 | 4.00 | |
| 4-Methylbenzylidenecamphor | | 2.00 | | 4.00 | 2.00 |
| Octocrylene | 7.00 | 2.50 | 4.00 | | 2.50 |
| Diethylhexylbutamidotriazone | 1.00 | | | 2.00 | |
| Phenylene-1,4-bis(monosodium, 2-benzimidazyl-5,7-disulfonic acid) | 1.00 | 2.00 | 0.50 | | |
| Phenylbenzimidazolesulfonic acid | 0.50 | | | 3.00 | 2.00 |
| Titanium dioxide | | 2.00 | 1.50 | | 3.00 |
| Zinc oxide | 3.00 | 1.00 | 2.00 | 0.50 | |
| Paraffinum liquidum | | | 10.0 | | 8.00 |
| $C_{12-15}$-alkyl benzoate | | | | 9.00 | |
| Dicaprylyl ether | 10.00 | | | | 7.00 |
| Butylene glycol dicaprylate/dicaprate | | | 2.00 | 8.00 | 4.00 |
| Dicaprylyl carbonate | 5.00 | | 6.00 | | |
| Dimethicone polydimethyl siloxane | | 4.00 | 1.00 | 5.00 | |
| Phenylmethylpolysiloxane | 2.00 | 25.00 | | | 2.00 |
| Shea butter | | | 3.00 | | |
| PVP hexadecene copolymer | 0.50 | | | 0.50 | 1.00 |
| Octoxyglycerol | | 0.30 | 1.00 | | 0.50 |
| Glycerol | 3.00 | 7.50 | | 7.50 | 2.50 |
| Glycine soya | | | 1.00 | 1.50 | |

III. Examples of W/O emulsions (continued)

| | | | | | |
|---|---|---|---|---|---|
| Magnesium sulfate | 1.00 | 0.50 | | 0.50 | |
| Magnesium chloride | | | 1.00 | | 0.70 |
| Tocopherol acetate | 0.50 | | 0.25 | | 1.00 |
| Uracil | 0.30 | 0.60 | 1.00 | 1.20 | 0.80 |
| Preservative | q.s. | q.s. | q.s. | q.s. | q.s. |
| Ethanol | 3.00 | | 1.50 | | 1.00 |
| Perfume | q.s. | q.s. | q.s. | q.s. | q.s. |
| Water | ad 100 | ad 100 | ad 100 | ad 100 | ad 100 |

| | 6 | 7 |
|---|---|---|
| Polyglyceryl-2 dipolyhydroxystearate | 4.00 | 5.00 |
| Lanolin alcohol | 0.50 | 1.50 |
| Isohexadecane | 1.00 | 2.00 |
| Myristyl myristate | 0.50 | 1.50 |
| Vaseline | 1.00 | 2.00 |
| 1-(4-tert-Butylphenyl)-3-(4-methoxyphenyl)-1,3-propanedione | 0.50 | 1.50 |
| 4-Methylbenzylidenecamphor | 1.00 | 3.00 |
| Butylene glycol dicaprylate/dicaprate | 4.00 | 5.00 |
| Shea butter | | 0.50 |
| Butylene glycol | | 6.00 |
| Octoxyglycerol | | 3.00 |
| Glycerol | 5.00 | |
| Tocopherol acetate | 0.50 | 1.00 |
| Uracil | 0.50 | 0.25 |
| Na$_3$HEDTA | 0.20 | 0.20 |
| Preservative | q.s. | q.s. |
| Ethanol | | 3.00 |
| Perfume | q.s. | q.s. |
| Water | ad 100.00 | ad 100.00 |

IV. Examples of hydrodispersions

| | 1 | 2 | 3 | 4 | 5 |
|---|---|---|---|---|---|
| Polyoxyethylene(20) cetylstearyl ether | 1.00 | | | 0.5 | |
| Cetyl alcohol | | | 1.00 | | |
| Sodium polyacrylate | | 0.20 | | 0.30 | |
| Acrylate/C$_{10-30}$-alkyl acrylate crosspolymer | 0.50 | | 0.40 | 0.10 | 0.10 |
| Xanthan gum | | 0.30 | 0.15 | | 0.50 |
| 2-Ethylhexyl methoxycinnamate | | | | 5.00 | 8.00 |
| 2,4-Bis-(4-(2-ethylhexyloxy)-2-hydroxy)-phenyl)-6-(4-methoxyphenyl)-(1,3,5)-triazine | | 1.50 | | 2.00 | 2.50 |
| 1-(4-tert-Butylphenyl)-3-(4-methoxyphenyl)-1,3-propanedione | 1.00 | | 2.00 | | |
| Diethylhexylbutamidotriazone | | 2.00 | | 2.00 | 1.00 |
| Ethylhexyltriazone | 4.00 | | 3.00 | 4.00 | |
| 4-Methylbenzylidenecamphor | 4.00 | 4.00 | | | 2.00 |
| Octocrylene | | 4.00 | 4.00 | | 2.50 |
| Phenylene-1,4-bis(sodium-2-benzimidazyl-5,7-disulfonic acid | 1.00 | | 0.50 | | 2.00 |
| Phenylbenzimidazolesulfonic acid | 0.50 | | | 3.00 | |
| Titanium dioxide | 0.50 | | 2.00 | 3.00 | 1.00 |
| Zinc oxide | 0.50 | 1.00 | 3.00 | | 2.00 |
| C$_{12-15}$-alkyl benzoate | 2.00 | 2.50 | | | |
| Dicaprylyl ether | | 4.00 | | | |
| Butylene glycol dicaprylate/dicaprate | 4.00 | | 2.00 | 6.00 | |
| Dicaprylyl carbonate | | | 2.00 | 6.00 | |
| Dimethicone polydimethylsiloxane | | | 0.50 | 1.00 | |
| Phenylmethylpolysiloxane | 2.00 | | | 0.50 | 2.00 |
| Shea butter | | 2.00 | | | |
| PVP Hexadecene copolymer | 0.50 | | | 0.50 | 1.00 |
| Octoxyglycerol | | | 1.00 | | 0.50 |
| Glycerol | 3.00 | 7.50 | | 7.50 | 2.50 |
| Glycine soya | | | 1.50 | | |
| Tocopherol acetate | 0.50 | | 0.25 | | 1.00 |
| Uracil | 0.25 | 0.60 | 1.00 | 0.70 | 0.80 |
| Preservative, perfume | q.s. | q.s. | q.s. | q.s. | q.s. |
| Ethanol | 3.00 | 2.00 | 1.50 | | 1.00 |
| Water | ad 100 | ad 100 | ad 100 | ad 100 | ad 100 |

| V. Example (gel cream): | |
|---|---|
| Acrylate/$C_{10-30}$-alkyl acrylate crosspolymer | 0.40 |
| Polyacrylic acid | 0.20 |
| Xanthan gum | 0.10 |
| Cetearyl alcohol | 3.00 |
| $C_{12-15}$-alkyl benzoate | 4.00 |
| Caprylic/capric triglyceride | 3.00 |
| Cyclic dimethylpolysiloxane | 5.00 |
| Dimethicone polydimethylsiloxane | 1.00 |
| Uracil | 0.30 |
| Glycerol | 3.00 |
| Sodium hydroxide | q.s. |
| Preservative | q.s. |
| Perfume | q.s. |
| Water | ad 100.0 |
| pH adjusted to 6.0 | |

| VI. Example (W/O cream) | |
|---|---|
| Polyglyceryl-3-diisostearate | 3.50 |
| Glycerol | 3.00 |
| Polyglyceryl-2 dipolyhydroxystearate | 3.50 |
| Purine | 0.50 |
| Preservative | q.s. |
| Perfume | q.s. |
| Magnesium sulfate | 0.6 |
| Isopropyl stearate | 2.0 |
| Caprylyl ether | 8.0 |
| Cetearyl isononanoate | 6.0 |
| Water | ad 100.0 |

What is claimed is:

1. A cosmetic or dermatological composition, wherein the composition is effective for at least one of boosting natural skin tanning and stimulating melanogenesis in human skin and comprises from 0.0001% to 20% by weight of at least one substance selected from pyrimidines and purines.

2. The composition of claim 1, wherein the at least one substance is present in a concentration of from 0.001% to 10% by weight.

3. The composition of claim 1, wherein the at least one substance is present in a concentration of from 0.01% to 1% by weight.

4. The composition of claim 1, wherein the composition comprises at least one of purine, uracil, thymine, adenine, guanine and cytosine.

5. The composition of claim 4, wherein the composition comprises purine.

6. The composition of claim 4, wherein the composition comprises uracil.

7. The composition of claim 4, wherein the composition comprises thymine.

8. The composition of claim 4, wherein the composition comprises adenine.

9. The composition of claim 4, wherein the composition comprises guanine.

10. The composition of claim 4, wherein the composition comprises cytosine.

11. The composition of claim 3, wherein the composition comprises uracil.

12. The composition of claim 11, wherein the composition comprises at least 0.1% by weight of uracil.

13. The composition of claim 1, wherein the composition further comprises at least one of a UVA filter and a UVB filter.

14. The composition of claim 1, wherein the composition further comprises an inorganic pigment.

15. The composition of claim 14, wherein the inorganic pigment comprises an oxide of at least one of Ti, Zn, Fe, Zr, Si, Mn, Al and Ce.

16. The composition of claim 15, wherein the inorganic pigment comprises $TiO_2$.

17. The composition of claim 2, wherein the composition further comprises at least one hydrophobic inorganic micropigment.

18. The composition of claim 3, wherein the composition further comprises from 0.5% to 6% by weight of at least one inorganic pigment.

19. The composition of claim 1, wherein the composition further comprises from 0.05% to 10% by weight of an antioxidant.

20. A sunscreen which comprises the composition of claim 4.

21. An O/W cream which comprises the composition of claim 2.

22. A W/O emulsion which comprises the composition of claim 2.

23. A gel cream which comprises the composition of claim 2.

24. A cosmetic or dermatological composition, wherein the composition is effective for at least one of boosting natural skin tanning and stimulating melanogenesis in human skin and comprises from 0.1% to 1% by weight of at least one of purine, uracil, thymine, adenine, guanine and cytosine.

25. The composition of claim 24, which further comprises at least one of a UVA filter and a UVB filter.

26. The composition of claim 24, wherein the composition further comprises a hydrophobic inorganic micropigment.

27. The composition of claim 25, wherein the composition comprises uracil.

28. A method for at least one of boosting natural skin tanning and stimulating melanogenesis in human skin, wherein the method comprises applying onto at least parts of the skin a composition which comprises at least one substance selected from pyrimidines and purines and wherein the at least one substance is effective for at least one of boosting natural skin tanning and stimulating melanogenesis in human skin.

29. The method of claim 28, wherein the at least one substance is present in a concentration of from 0.0001% to 20% by weight.

30. The method of claim 28, wherein the at least one substance is present in a concentration of from 0.01% to 1% by weight.

31. The method of claim 29, wherein the composition comprises at least one of purine, uracil, thymine, adenine, guanine and cytosine.

32. The method of claim 28, wherein the composition comprises purine.

33. The method of claim 28, wherein the composition comprises uracil.

34. The method of claim 28, wherein the composition comprises thymine.

35. The method of claim 28, wherein the composition comprises adenine.

36. The method of claim 28, wherein the composition comprises guanine.

37. The method of claim 28, wherein the composition comprises cytosine.

38. The method of claim 30, wherein the composition comprises at least 0.1% by weight of uracil.

39. The method of claim 28, wherein the composition comprises an emulsion.

40. The method of claim 28, wherein the method comprises a treatment of hypopigmentation.

* * * * *